(12) United States Patent
Zhang et al.

(10) Patent No.: US 7,607,363 B2
(45) Date of Patent: Oct. 27, 2009

(54) LIQUID VOLUME METERING DEVICE AND METHOD

(75) Inventors: Yaohui Zhang, Shenzhen (CN); Cheng Zhang, Shenzhen (CN); Liangqing Li, Shenzhen (CN)

(73) Assignee: Shenzhen Mindray Bio-Medical Electronics Co., Ltd. (CN)

( * ) Notice: Subject to any disclaimer, the term of this patent is extended or adjusted under 35 U.S.C. 154(b) by 0 days.

(21) Appl. No.: 11/530,388

(22) Filed: Sep. 8, 2006

(65) Prior Publication Data

US 2007/0269882 A1    Nov. 22, 2007

(30) Foreign Application Priority Data

May 17, 2006    (CN)    .................. 2006 1 0035551

(51) Int. Cl.
*G01N 1/14*    (2006.01)
*B67D 5/16*    (2006.01)

(52) U.S. Cl. ...................... 73/864.34; 222/71
(58) Field of Classification Search ................ 73/864, 73/864.34, 864.35, 64; 222/71
See application file for complete search history.

(56) References Cited

U.S. PATENT DOCUMENTS

| | | | | |
|---|---|---|---|---|
| 1,873,010 | A | * | 8/1932 | Mitton ............... 73/864.35 |
| 2,995,037 | A | * | 8/1961 | Parker et al. ........ 73/864.35 |
| 3,015,957 | A | * | 1/1962 | Paulson et al. ....... 73/864.34 |
| 3,209,598 | A | * | 10/1965 | Anderson et al. ..... 73/864.35 |
| 3,587,670 | A | * | 6/1971 | Brailsford .......... 73/864.35 |
| 3,693,436 | A | * | 9/1972 | Gildner ............. 73/861.05 |
| 3,720,109 | A | * | 3/1973 | Blechman ........... 73/864.35 |

(Continued)

FOREIGN PATENT DOCUMENTS

CN    85204477 U    9/1986

(Continued)

OTHER PUBLICATIONS

Chinese Search Report dated Jun. 1, 2006 for Chinese patent application No. 200610035551.7.

(Continued)

*Primary Examiner*—David A. Rogers
(74) *Attorney, Agent, or Firm*—Vista IP Law Group, LLP.

(57) ABSTRACT

The present invention discloses a liquid volumetric device comprising a metering tube, a start sensor, an end sensor, a bath for storage of a sample to be metered, a vacuum chamber and a pump for pumping out air inside the vacuum chamber to form a negative pressure inside the vacuum chamber. The start sensor and the end sensor are provided respectively at the bottom and the top of the metering tube, the top of the metering tube is in communication respectively with the vacuum chamber and the outside atmosphere via pipelines, the bottom of the metering tube is in communication respectively with the bath and the vacuum chamber via pipelines, and control parts are provided in each of the pipelines for controlling connection/disconnection thereof. Thus, by forming a negative pressure inside the vacuum chamber, a sample in the bath may be pressed from down to up into the metering tube by means of a pressure difference between the atmosphere and the negative pressure, so as to complete the volume metering, whereby an occurrence of the side flow phenomenon can be completely eliminated.

13 Claims, 5 Drawing Sheets

U.S. PATENT DOCUMENTS

| | | | | |
|---|---|---|---|---|
| 3,769,841 A | * | 11/1973 | Thulin | 222/445 |
| 3,812,890 A | * | 5/1974 | Haas et al. | 141/94 |
| 3,895,534 A | * | 7/1975 | Stone | 73/864.34 |
| 3,901,653 A | * | 8/1975 | Jones et al. | 222/71 |
| 3,949,611 A | * | 4/1976 | Watt | 73/864.35 |
| 4,077,263 A | * | 3/1978 | Brailsford | 73/864.35 |
| 4,083,252 A | * | 4/1978 | Stookey | 73/864.35 |
| 4,215,573 A | * | 8/1980 | Tufts | 73/255 |
| 4,638,675 A | * | 1/1987 | Sperinck et al. | 73/864.34 |
| 4,688,435 A | * | 8/1987 | Welch | 73/864.34 |
| 5,099,698 A | * | 3/1992 | Kath et al. | 73/861.56 |
| 5,437,201 A | * | 8/1995 | Krueger | 73/864.35 |
| 2003/0066347 A1 | | 4/2003 | Goloby | |

FOREIGN PATENT DOCUMENTS

FR      2756628 A1 * 6/1998

OTHER PUBLICATIONS

Chinese Office Action dated Jul. 4, 2008 for Chinese patent application No. 200610035551.7.
English translation of abstracts for CN85204477U reference above.
English translation of abstracts for FR2756628 reference above.

* cited by examiner

LIQUID VOLUME METERING DEVICE AND METHOD

FIELD OF THE INVENTION

The present invention relates to the field of liquid volume metering, and particularly to a liquid volumetric device and method applied in a hemacytometer.

BACKGROUND OF THE INVENTION

Currently, for a hemacytometer which performs volume metering with the use of a metering tube, both detecting the surface of a liquid with an optical sensor and detecting a floater with an optical sensor share the same principle that a change in light intensity caused by an object such as the liquid or the floater can be utilized to control a start or an end of the volume metering.

The principle for detecting a liquid surface with an optical sensor is described hereinafter. There are two optical sensors, a start sensor and an end sensor, provided respectively at the top and the bottom of a metering tube. When the liquid surface passes the start sensor at the top of the metering tube, the presence of the liquid surface causes a change in light intensity, and hence an electrical signal is generated resulting in the start of the volume metering/counting; when the liquid surface reaches the end sensor at the bottom of the metering tube, there is a change in light intensity at the end sensor, and hence another electrical signal is generated resulting in the end of the volume metering/counting. For this metering mode, there may be a problem of liquid side flow for a reagent in the metering tube due to the self-gravity of the liquid, that is, the liquid flows down quickly along a certain side of the inner wall of the metering tube, which causes the metering cannot be performed. In order to reduce the probability of side flow, a rinse with a relatively great surface tension has to be used in the metering tube for a cleanout and maintenance thereof. However, the side flow phenomenon may still occur when the metering tube dirties.

The principle for detecting a floater with an optical sensor is described hereinafter. When the floater passes the start sensor at the top of the metering tube, an electrical signal is generated resulting in the start of the volume metering/counting; when the floater reaches the end sensor at the bottom of the metering tube, another electrical signal is generated resulting in the end of the volume metering/counting. For this metering mode, although a relatively high metering precision may be achieved and the cleanout of the metering tube by the rinse may be avoided, the cost of the floater is rather high and the relevant cleanout is troublesome.

SUMMARY OF THE INVENTION

Accordingly, an object of the present invention is to overcome the above deficiencies in the prior art by providing a liquid volumetric device and method which can eliminate an occurrence of the side flow.

In order to achieve the above object and according to an aspect of the present invention, there is provided a liquid volumetric device which may comprise a metering tube, a start sensor, an end sensor, a bath for storage of a sample to be metered, a vacuum chamber and a pump for pumping out air inside the vacuum chamber to form a negative pressure inside the vacuum chamber. The start sensor and the end sensor may be provided respectively at the bottom and the top of the metering tube, the top of the metering tube may be in communication respectively with the vacuum chamber and the outside atmosphere via pipelines, the bottom of the metering tube may be in communication respectively with the bath and the vacuum chamber via pipelines, and control parts may be provided in each of the pipelines for controlling connection/disconnection thereof.

Preferably, the control part in the pipeline between the metering tube, the vacuum chamber and the outside atmosphere may be a three-way solenoid valve with a common port being in communication with the top of the metering tube and another two ports being respectively in communication with the vacuum chamber and the outside atmosphere, and the control part among the bottom of the metering tube, the vacuum chamber and the bath may be another three-way solenoid valve with a common port being in communication with the bottom of the metering tube and another two ports being respectively in communication with the vacuum chamber and the bath.

Preferably, the control part in the pipeline between the metering tube and the outside atmosphere may be a two-way solenoid valve, the control part in the pipeline between the vacuum chamber, the top of the metering tube and the bottom of the metering tube may be a three-way solenoid valve with a common port being in communication with the vacuum chamber and another two ports being respectively in communication with the top and the bottom of the metering tube, and the control part in the pipeline between the bottom of the metering tube and the bath may be another two-way solenoid valve.

Preferably, a filter may be provided in the pipeline between the top of the metering tube and the outside atmosphere.

Preferably, the bath may comprise a rear bath and a front bath, which are in communication with each other via an aperture.

Preferably, the rear bath may be in communication with a diluent vessel via a pipeline, the front bath may be in communication with the vacuum chamber via another pipeline, and two-way solenoid valves may be provided in each of the two pipelines for controlling connection/disconnection thereof.

Preferably, between the vacuum chamber and the pump there may be provided a three-way solenoid valve with a common port being in communication with one port of the pump and another two ports being respectively in communication with the vacuum chamber and a filter, and the other port of the pump may be in communication with a common port of another three-way solenoid valve with another two ports being respectively in communication with the outside atmosphere and the vacuum chamber.

According to another aspect of the present invention, there is provided a liquid volumetric method which may comprise the steps of:

a) establishing a first channel between the top of a metering tube and a vacuum chamber and a second channel between the bottom of the metering tube and a bath;

b) pumping out air inside the vacuum chamber through a pump to form a negative pressure inside the vacuum chamber, so as to press a sample in the bath to the bottom of the metering tube via the second channel by means of a pressure difference between the atmosphere and the negative pressure; and c) starting a counting measurement when a liquid surface of the sample reaches a start sensor at the bottom of the metering tube, and ending the counting measurement and closing the first channel and the second channel when the liquid surface of the sample reaches an end sensor at the top of the metering tube.

Preferably, before the step a), the method may further comprise the steps of:

d) filling the metering tube with a diluent, and establishing a third channel between the top of the metering tube and the outside atmosphere and a fourth channel between the bottom of the metering tube and the vacuum chamber;

e) pumping out the air inside the vacuum chamber to form a pressure difference between the vacuum chamber and the atmosphere, and enabling the diluent to flow from up to down through the metering tube so as to be drained into the vacuum chamber by means of the pressure difference and the gravity of the diluent;

f) switching between opening and closing of the third channel to drain residual liquid drops on an inner wall of the metering tube into the vacuum chamber by means of the pressure difference; and g) closing the third channel and the fourth channel.

Preferably, after the step c), the method may further comprise the steps of:

h) opening the third channel and the fourth channel to drain the sample in the metering tube from up to down into the vacuum chamber by means of a pressure difference between residual negative pressure in the vacuum chamber and the atmosphere as well as the gravity of the sample; and i) closing the third channel and the fourth channel and opening the first channel to press the diluent from a diluent vessel into a rear bath so as to flow from down to up into the metering tube by means of the pressure difference between the negative pressure in the vacuum chamber and the atmosphere, thereby accomplishing cleanout of the rear bath and the metering tube.

The present invention can be advantageous in that by forming a negative pressure inside the vacuum chamber, a sample in the bath may be pressed from down to up into the metering tube by means of a pressure difference between the atmosphere and the negative pressure, so as to complete the volume metering, whereby an occurrence of the side flow phenomenon can be completely eliminated.

DETAILED DESCRIPTION OF THE EMBODIMENTS

With reference to FIGS. 1-4, a liquid volumetric device according to an embodiment of the present invention includes a volumetric board 9, a vacuum chamber 8 and a bath 13. The volumetric board 9 comprises a start sensor 10, an end sensor 11 and a metering tube 12, and both the start sensor 10 and the end sensor 11 are optical sensors. The material of the metering tube 12 can be glass or any other transparent material, and this material may not react chemically with a liquid which flows through the metering tube 12, and meanwhile must ensure that the two optical sensors 10 and 11 are capable of detecting precisely whether the surface of the liquid arrives, namely a change in light intensity. The start sensor 10 is provided at the bottom of the metering tube 12, and the end sensor 11 is provided at the top thereof. The vacuum chamber 8 is used for a negative-pressure storage and functions as a temporary storage pool for waste liquid. Also, the vacuum chamber 8 is connected with a pump 7 which pumps out the air inside the vacuum chamber 8 resulting in a negative pressure therein. The bath 13 comprises a front bath 14, a rear bath 15 and an aperture 16 communicating the front and rear baths.

Figure 1:
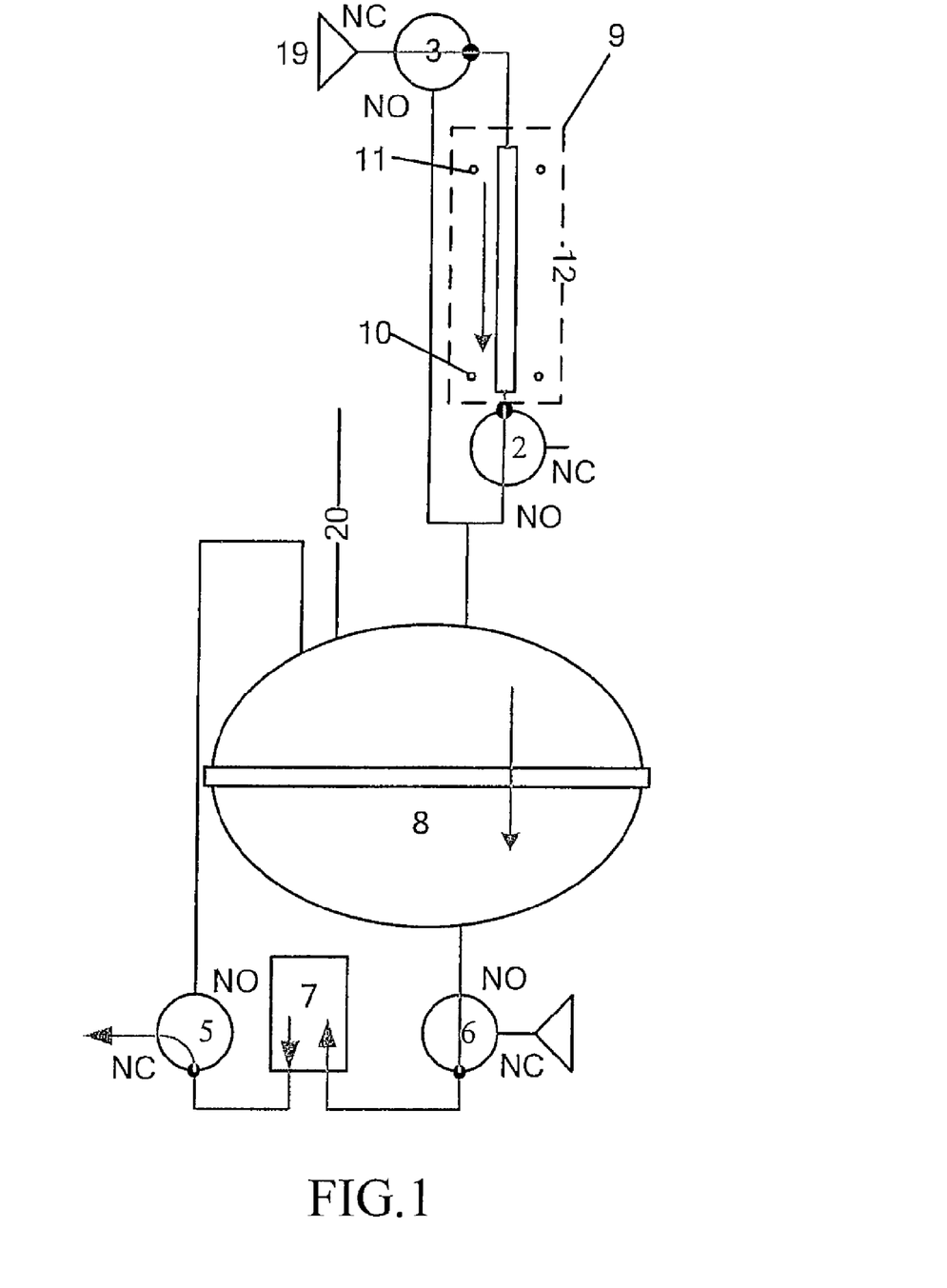
FIG. 1 is a structural principle diagram of the liquid volumetric device according to an embodiment of the present invention in the case of draining a metering tube.
Figure 2:
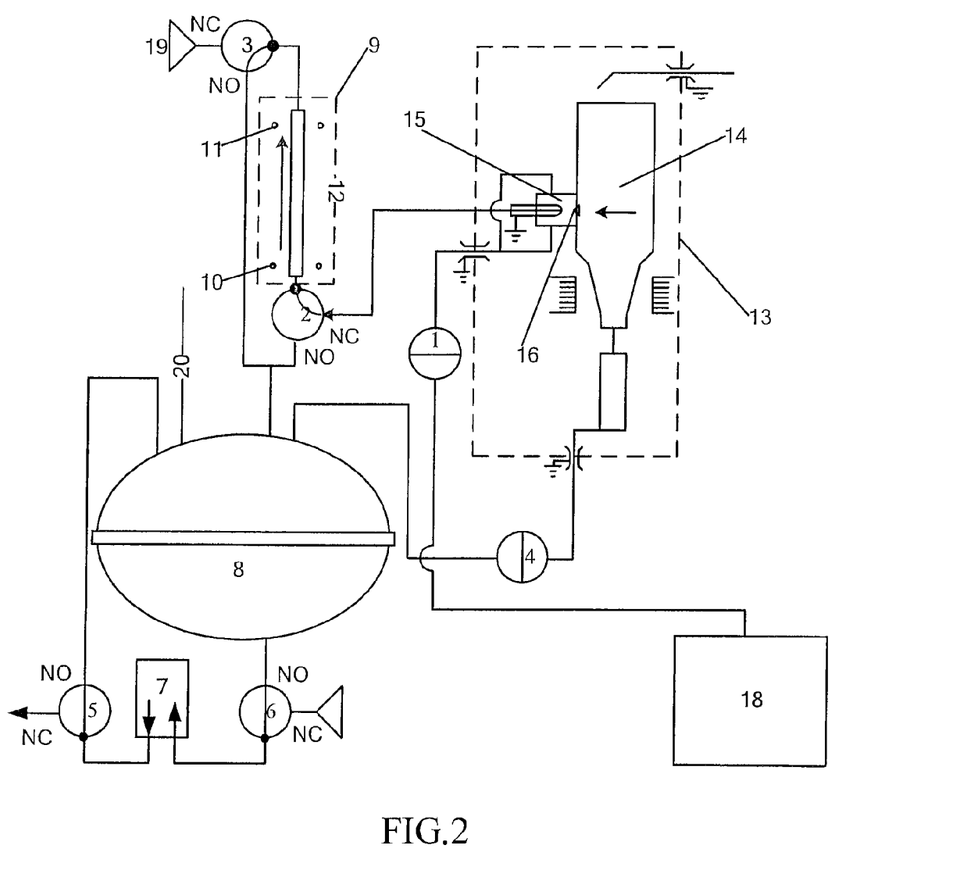
FIG. 2 is a structural principle diagram of the liquid volumetric device according to the embodiment of the present invention in the case of metering or counting.
Figure 3:
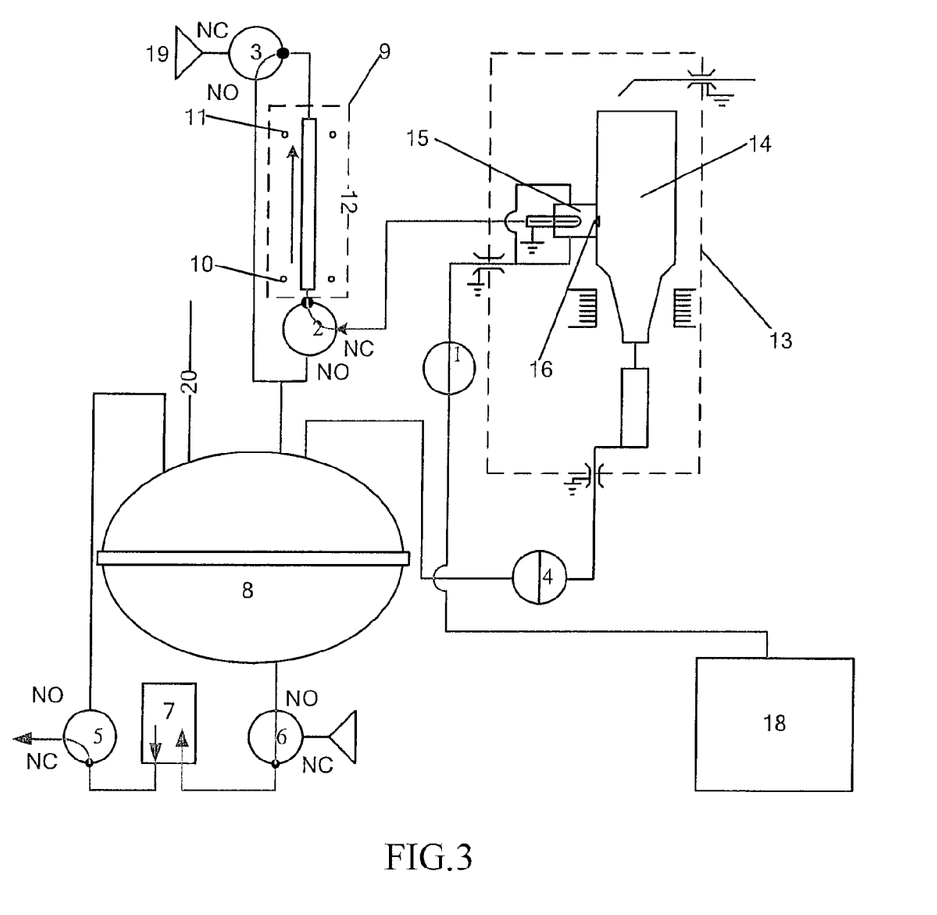
FIG. 3 is a structural principle diagram of the liquid volumetric device according to the embodiment of the present invention in the case of cleaning the metering tube.
Figure 4:
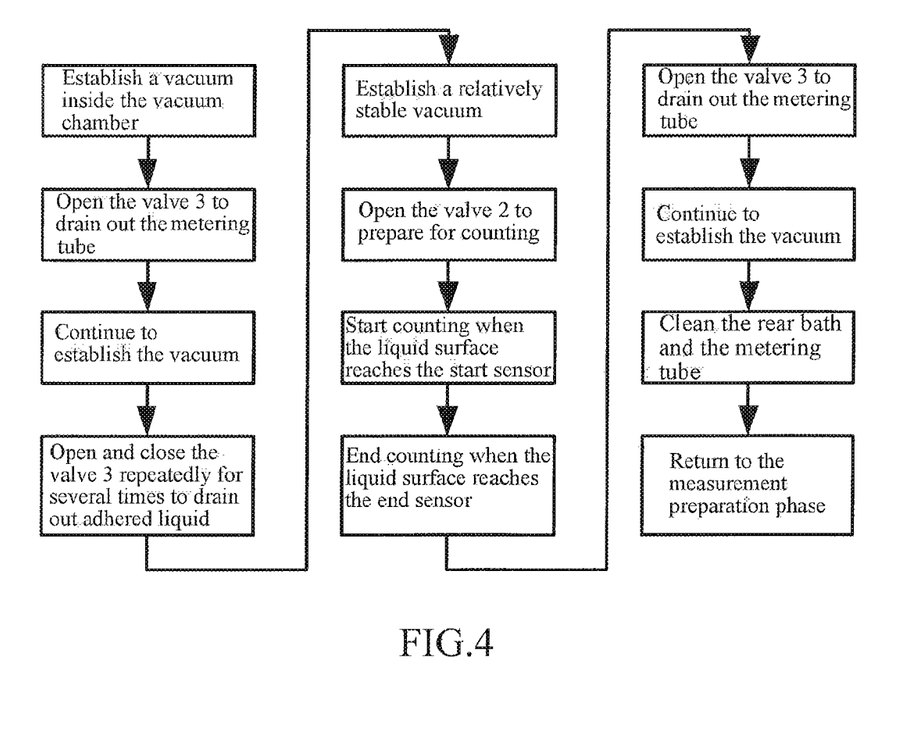
FIG. 4 is an operational flow chart of the liquid volumetric device according to the embodiment of the present invention.

The top of the metering tube 12 is connected with a third solenoid valve 3 which is a three-way solenoid valve, with a common port being in communication with the top of the metering tube 12, a normally closed port (NC) being in communication with a filter 19 that communicates with the outside atmosphere and is used for preventing dusts in the air from entering into the metering tube 12, and a normally open port (NO) being in communication with the vacuum chamber 8. The bottom of the metering tube 12 is connected with a second solenoid valve 2 which is a three-way solenoid valve, with a common port being in communication with the bottom of the metering tube 12, a normally closed port being in communication with the rear bath 15, and a normally open port being in communication with the vacuum chamber 8. The rear bath 15 is connected via a pipeline with a diluent vessel 18 for storage of a diluent, and a first solenoid valve 1 which is a two-way solenoid valve is provided in the pipeline for controlling connection/disconnection of the pipeline. The bottom of the front bath 14 is connected with the vacuum chamber 8 via a pipeline in which a fourth solenoid valve 4 which is a two-way solenoid valve is provided for controlling connection/disconnection of the pipeline. The bottom of the vacuum chamber 8 is connected with a sixth solenoid valve 6 which is a three-way solenoid valve, with a common port being in communication with one port of the pump 7, a normally open port being in communication with the bottom of the vacuum chamber 8, and a normally closed port being in communication with a filter. The other port of the pump 7 is connected with a fifth solenoid valve 5 which is a three-way solenoid valve, with a common port being in communication with the other port of the pump 7, a normally open port being in communication with the top of the vacuum chamber 8, and a normally closed port being in communication with the outside atmosphere. In addition, the vacuum value of the vacuum chamber 8 is monitored in real time by a pressure sensor 20. When the pressure sensor 20 detects that the vacuum value inside the vacuum chamber 8 reaches a desired value, the fifth solenoid valve 5 and the pump 7 cease to operate. In this embodiment, in the case of volume metering, the first, the second, the third, the fourth, the fifth and the six solenoid valves are respectively in a closed position, a normally closed position (namely the common port being in communication with the normally closed port), a normally open position (namely the common port being in communication with the normally open port), a closed position, a normally open position and a normally open position; and in the case of draining out the metering tube 12 after the volume metering is completed, the first, the second, the third, the fourth, the fifth and the six solenoid valves are respectively in a closed position, a normally open position, a normally closed position, a closed position, a normally closed position and a normally open position.

An operational procedure of the liquid volumetric device is described as following.

1. Draining the Metering Tube

The fifth solenoid valve 5 and the pump 7 start to operate (that is, the fifth solenoid valve 5 is opened), so as to establish a vacuum inside the vacuum chamber 8. The third solenoid valve 3 is opened, the metering tube 12 full of the diluent communicates with the outside atmosphere via the normally closed port (NC) of the third solenoid valve 3, and the diluent in the metering tube 12 is drained quickly from up to down into the vacuum chamber 8 via the normally open port (NO) of the second solenoid valve 2 by means of a pressure difference between the atmosphere and a negative pressure of the vacuum chamber 8. Since the filter 19 is installed at the normally closed port of the third solenoid valve 3, dusts in the air can be prevented from entering into the metering tube 12 via the normally closed port of the third solenoid valve 3 when the third solenoid valve 3 is opened, so as not to pollute the inner wall of the metering tube 12.

The fifth solenoid valve 5 and the pump 7 continue to operate, the liquid and the air in the vacuum chamber 8 are drained from the normally open port of the sixth solenoid valve 6 to the outside of the device via the pump 7 and the normally closed port of the fifth solenoid valve 5, and meanwhile a vacuum is established inside the vacuum chamber 8. After a water film adhered to the inner wall of the metering tube 12 gathers as liquid drops at the inner wall, the third solenoid valve 3 is opened, and those liquid drops with relatively large volumes adhered to the inner wall of the metering tube 12 are drained by means of the pressure difference. Then the third solenoid valve 3 is closed, and the fifth solenoid valve 5 and the pump 7 continue to operate so as to establish a vacuum while repeating for several times the rapid opening and closing of the third solenoid valve 3 at a certain time interval. In this way, those tiny liquid drops adhered to the inner wall of the metering tube 12 can be drained completely to prepare for a counting measurement. The time interval at which the third solenoid valve is opened and closed and the vacuum value established in the vacuum chamber in the case of draining the liquid drops with relatively large volumes adhered to the inner wall of the metering tube are respectively different from the time interval and the vacuum value in the case of draining the liquid drops with relatively small volumes. Therefore, the liquid drops which are adhered to the inner wall of the metering tube and vary in volume can be drained in batches at different time-points.

2. Metering the Liquid Volume

The procedure goes to a counting preparation phase after the metering tube 12 is drained. The fifth solenoid valve 5 and the pump 7 start to operate (that is, the fifth solenoid valve 5 is opened), the liquid and air in the vacuum chamber 8 are drained from the normally open port of the sixth solenoid valve 6 to the outside of the device via the pump 7 and the normally closed port of the fifth solenoid valve 5, and meanwhile a negative pressure is established and stored in the vacuum chamber 8, where the vacuum value is monitored in real time by the pressure sensor 20. When the pressure sensor 20 detects that the vacuum value in the vacuum chamber 8 reaches a negative pressure value desired for the counting, the sixth solenoid valve 6 and the pump 7 cease to operate. The second solenoid valve 2 is opened to be in the normally closed position (that is, the common port is in communication with the normally closed port), and the metering tube 12 with no liquid therein is in communication with the rear bath 15 via the normally closed port of the second solenoid valve 2. At this time, a sample in the front bath 14 enters into the rear bath 15 via the aperture 16 under the effect of the pressure difference between the atmosphere and the vacuum chamber 8.

When the sample reaches the start sensor 10 at the bottom of the metering tube 12 via the rear bath 15 under the effect of the pressure difference, an optical signal is generated, and at the same time the counting preparation phase ends and the procedure goes to a counting measurement phase. When the liquid surface reaches the end sensor 11 at the top of the metering tube 12, another optical signal is generated, the second solenoid valve 2 is closed, and the counting measurement phase ends with the volume metering completed.

3. Cleaning the Metering Tube

The third solenoid valve 3 is opened, and the liquid in the metering tube 12 is drained to the vacuum chamber 8 via the normally open port of the second solenoid valve 2 by means of a pressure difference between the residual negative pressure in the vacuum chamber 8 and the atmosphere as well as the self-gravity of the liquid in the metering tube 12. Next, the fifth solenoid valve 5 and the pump 7 start to operate. The liquid in the vacuum chamber 8 is drained from the normally open port of the sixth solenoid valve 6 to the outside of the device via the pump 7 and the normally closed port of the fifth solenoid valve 5, and then a vacuum is to be established.

The first solenoid valve 1 is opened, and the diluent enters into the rear bath 15 via the first solenoid valve 1 under the effect of a pressure difference, firstly cleaning the rear bath 15, and then passing through the second solenoid valve 2 from the rear bath 15 to enter into the metering tube 12 and clean it from down to up. Upon cleanout of the metering tube 12, the first, the second and the fifth solenoid valves 1, 2 and 5 and the pump 7 cease to operate. The cleaning of the metering tube is thus completed, and the procedure returns to a measurement preparation phase.

Figure 5:
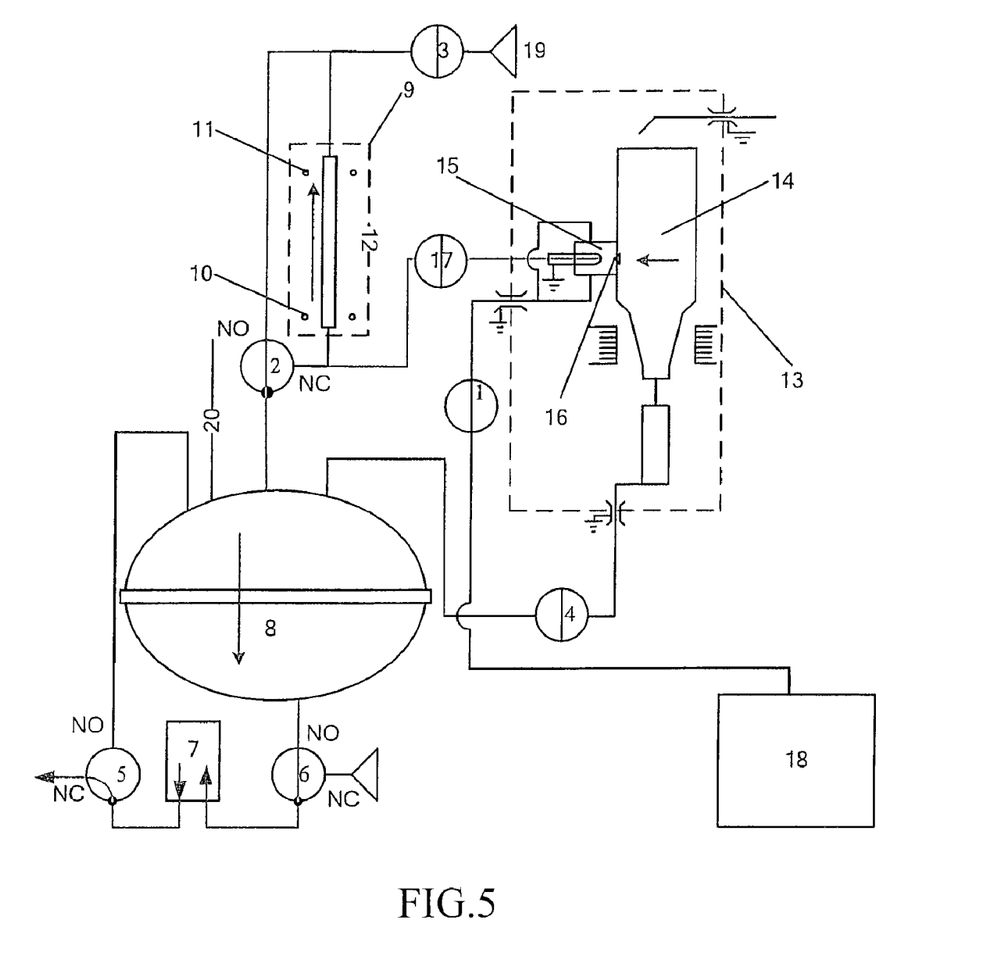
FIG. 5 is a structural principle diagram of the liquid volumetric device according to another embodiment of the present invention.

With reference to FIG. 5, another embodiment of the present invention is illustrated. In this embodiment, a third solenoid valve 3 which is a two-way solenoid valve is provided in the pipeline between the top of the metering tube 12 and the filter 19, the vacuum chamber 8 is in communication with the common port of the second solenoid valve 2, the normally open port of which is in communication with the top of the metering tube 12 and the normally closed port of which is in communication with the bottom of the metering tube 12, and a solenoid valve 17 which is a two-way solenoid valve is provided in the pipeline between the metering tube 12 and the rear bath 15. The operational principle for this liquid volumetric device is the same as that described in the previous embodiment. This device not only ensures that the liquid flows through the metering tube from down to up, but also enables a significant reduction in the time of metering preparation.

In the present invention, by repeatedly opening and closing for several times of solenoid valves at different time intervals and by means of various pressure differences, liquid drops with relatively large volumes are drained out firstly, and then liquid drops with relatively small volumes are drained out, so as to reduce the effect on the volume metering due to residual liquid drops. Since such a from-down-to-up volumetric mode is adopted, an occurrence of the side flow can be completely eliminated, and it is also possible to eliminate the necessities of wiping instruments and rinse and to reduce the number of reagent types, the cost of a single sample and the cost of the device.

While the present invention has been further illustrated and described with reference to some particularly preferred embodiments thereof, the present invention should not be construed as being limited to those embodiments. It should be understood for those skilled in the art that various modifications, variations and changes can be made without departing from the concept and spirit of the present invention, and that all the modifications, variations and changes should be regarded as being contained within the scope of the present invention as defined by the accompanied claims.

What is claimed is:

1. A liquid volumetric device comprising a metering tube, a start sensor, an end sensor and a bath for storage of a sample to be metered, wherein the device further comprises:
   a vacuum chamber; and
   a pump for pumping out gas inside the vacuum chamber to form a negative pressure inside the vacuum chamber, wherein
      a start sensor and an end sensor respectively connect directly or indirectly to a lower portion and an upper portion of a metering tube,
      the upper portion of the metering tube connects directly or indirectly to the vacuum chamber and outside atmosphere,
      the lower portion of the metering tube connects directly or indirectly to a bath and the vacuum chamber, and
      at least one control mechanism for controlling flow or operation of the liquid volumetric device, wherein the at least one control mechanism comprises:
         a first valve comprising a common port which connects directly or indirectly to an upper portion of the metering tube, and two additional ports which respectively connect directly or indirectly to the vacuum chamber and the outside atmosphere, and
         a second valve comprising a common port which connects directly or indirectly to the lower portion of the metering tube and two additional ports which respectively connect directly or indirectly to the vacuum chamber and the bath.

2. The liquid volumetric device according to claim 1, wherein the at least one control mechanism further comprises:
   a third valve comprising a common port which connects directly or indirectly to the vacuum chamber and two additional ports which respectively connect directly or indirectly to the upper portion and the lower portion of the metering tube.

3. The liquid volumetric device according to claim 1, wherein a first filter is located between the upper portion of the metering tube and the outside atmosphere.

4. The liquid volumetric device according to claim 1, wherein the at least one control mechanism further comprises:
   a sixth valve comprising two ports which respectively connect directly or indirectly to the metering tube and the outside atmosphere.

5. The liquid volumetric device according to claim 1, further comprising:
   an eighth valve, located between the vacuum chamber and the pump, comprising a common port which connects directly or indirectly to a first port of the pump and two additional ports which respectively connect to the vacuum chamber and a third filter, wherein
      the pump comprises a second port which connects directly or indirectly to a common port of another valve with two additional ports which respectively connect directly or indirectly to the outside atmosphere and the vacuum chamber.

6. The liquid volumetric device according to claim 1, further comprises:
   a tenth valve, located between the vacuum chamber and the pump, with a common port connecting directly or indirectly to a third port of the pump, and two additional ports respectively connecting to the vacuum chamber and a fourth filter, wherein
      a fourth port of the pump connects directly or indirectly to a common port of an eleventh valve with at least two ports which respectively connect directly or indirectly to the outside atmosphere and the vacuum chamber.

7. The liquid volumetric device claim 1, wherein the at least one control mechanism further comprises:
   a fourth valve comprising two ports which connect directly or indirectly to the lower portion of the metering tube and the bath.

8. The liquid volumetric device according to claim 1, wherein the bath comprises a rear bath and a front bath which are connected with each other via an aperture.

9. The liquid volumetric device according to claim 8, wherein the rear bath is connected directly or indirectly to a diluent vessel with a fifth valve comprising two ports for controlling an operation of or a flow between the rear bath and the diluent vessel.

10. The liquid volumetric device according to claim 8, wherein
    the front bath is connected directly or indirectly to the vacuum chamber with a seventh valve comprising two ports for controlling an operation of or a flow between the rear bath and the diluent vessel.

11. A liquid volumetric method, comprising:
    establishing a first channel between a top of a metering tube and a vacuum chamber and a second channel between a bottom of the metering tube and a bath;
    pumping out gas inside the vacuum chamber through a pump to form a negative pressure inside the vacuum chamber, so as to press a sample in the bath to the bottom of the metering tube via the second channel by causing a pressure difference between atmosphere and the negative pressure; and
    starting a counting measurement when a liquid surface of the sample reaches a start sensor at the bottom of the metering tube, and ending the counting measurement and closing the first channel and the second channel when the liquid surface of the sample reaches an end sensor at the top of the metering tube.

12. The liquid volumetric method according to claim 11, wherein before the act of establishing the first channel, the method further comprises:
    filling the metering tube with a diluent, and establishing a third channel between the top of the metering tube and the atmosphere and a fourth channel between the bottom of the metering tube and the vacuum chamber;
    pumping out the gas inside the vacuum chamber to form a pressure difference between the vacuum chamber and the atmosphere, and causing the diluent to flow through the metering tube so as to be drained into the vacuum chamber by the pressure difference and gravity;
    switching between opening and closing of the third channel to drain a residual of the diluent on an inner wall of the metering tube into the vacuum chamber by the pressure difference; and
    closing the third channel and the fourth channel.

13. The liquid volumetric method according to claim 12, wherein after the act of starting the counting measurement, the method further comprises:
    opening the third channel and the fourth channel to drain the sample in the metering tube into the vacuum chamber by the pressure difference between the negative pressure in the vacuum chamber and the atmosphere and the gravity; and closing the third channel and the fourth channel and opening the first channel to cause the diluent to flow from a diluent vessel into the metering tube by the pressure difference so as to clean the rear bath and the metering tube.

* * * * *